(12) United States Patent
He et al.

(10) Patent No.: US 9,585,579 B2
(45) Date of Patent: Mar. 7, 2017

(54) SYSTEMS AND METHODS FOR NONINVASIVE SPECTRAL-SPATIOTEMPORAL IMAGING OF CARDIAC ELECTRICAL ACTIVITY

(71) Applicants: Bin He, Arden Hills, MN (US); Zhaoye Zhou, Minneapolis, MN (US)

(72) Inventors: Bin He, Arden Hills, MN (US); Zhaoye Zhou, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 183 days.

(21) Appl. No.: 14/266,001

(22) Filed: Apr. 30, 2014

(65) Prior Publication Data

US 2014/0323848 A1 Oct. 30, 2014

Related U.S. Application Data

(60) Provisional application No. 61/817,710, filed on Apr. 30, 2013.

(51) Int. Cl.

| A61B 5/0476 | (2006.01) |
|---|---|
| A61B 5/04 | (2006.01) |
| A61B 5/046 | (2006.01) |
| A61B 5/0432 | (2006.01) |
| A61B 6/00 | (2006.01) |
| A61B 5/00 | (2006.01) |
| A61B 5/055 | (2006.01) |
| A61B 6/03 | (2006.01) |

(52) U.S. Cl.
CPC .......... *A61B 5/04012* (2013.01); *A61B 5/046* (2013.01); *A61B 5/0432* (2013.01); *A61B 5/0037* (2013.01); *A61B 5/0044* (2013.01); *A61B 5/055* (2013.01); *A61B 5/7278* (2013.01); *A61B 5/7289* (2013.01); *A61B 6/032* (2013.01); *A61B 6/507* (2013.01); *A61B 2576/023* (2013.01)

(58) Field of Classification Search
CPC ... A61B 5/004; A61B 5/0422; A61B 5/04012; A61B 5/046; A61B 5/0432; A61B 5/0037; A61B 5/0044; A61B 5/055; A61B 5/7289; A61B 5/7278; A61B 6/503; A61B 6/5247; A61B 8/0883; A61B 2018/00839; G06K 9/0057
See application file for complete search history.

(56) References Cited

U.S. PATENT DOCUMENTS

| 9,220,429 B2* | 12/2015 | Nabutovsky ....... A61B 5/04014 |
|---|---|---|
| 2007/0270703 A1* | 11/2007 | He ....................... A61B 5/0422 600/509 |
| 2012/0089038 A1* | 4/2012 | Ryu ....................... A61B 5/046 600/515 |

* cited by examiner

*Primary Examiner* — Elmer Chao
(74) *Attorney, Agent, or Firm* — Quarles & Brady LLP

(57) ABSTRACT

A system and method for non-invasively generating a report of cardiac electrical activities of a subject includes determining, using cardiac electrical activation information, equivalent current densities (ECDs). The ECDs are assembled into time-course ECD information and a spectrum of the time-course ECD information is analyzed to determine peaks for spectral characteristics of atrial fibrillation (AF). The spectral characteristics of AF are correlated with potential electrical sources of the AF and a report is generated indicating the potential electrical sources of the AF spatially registered with the medical imaging data.

21 Claims, 10 Drawing Sheets

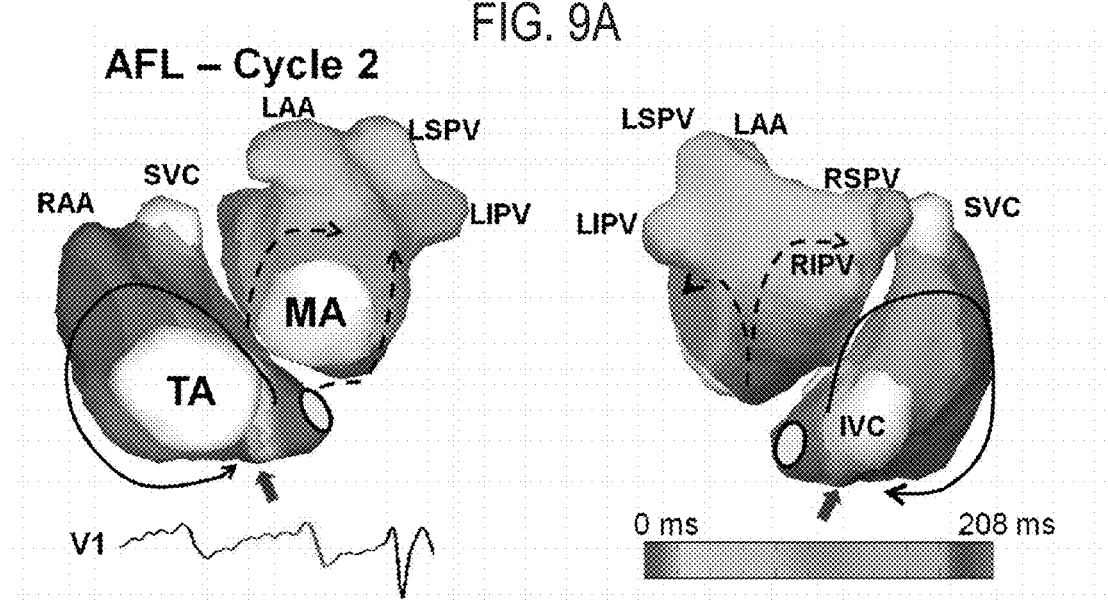
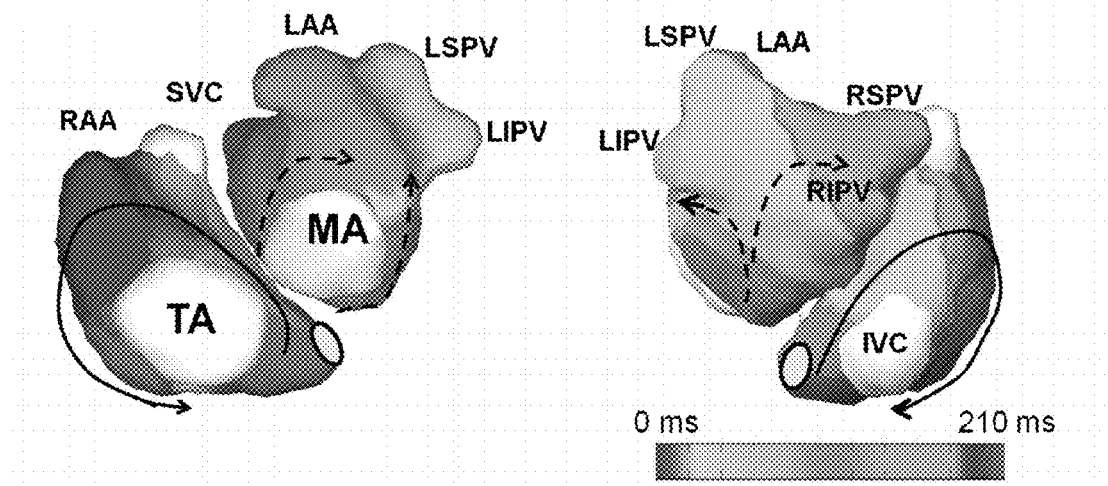

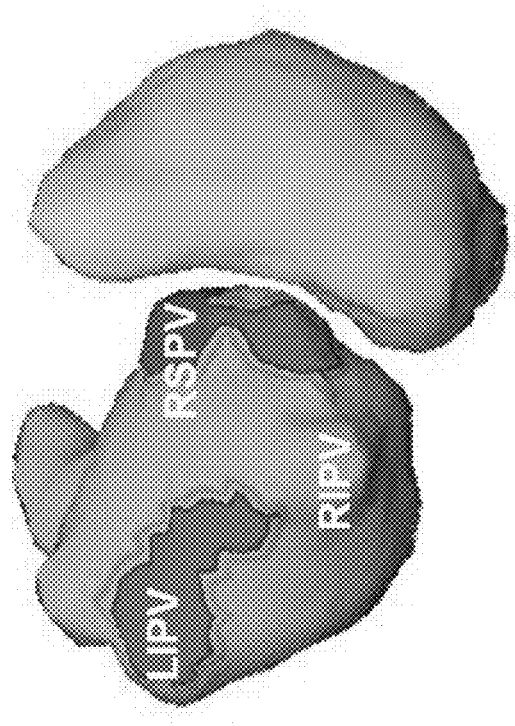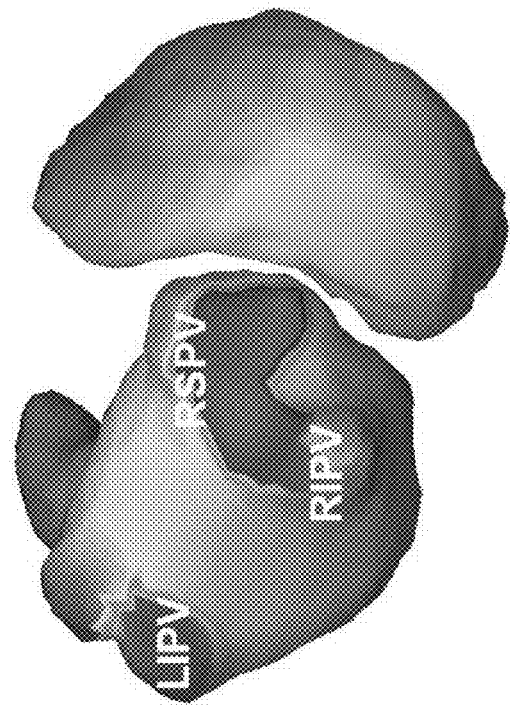
FIG. 11

SYSTEMS AND METHODS FOR NONINVASIVE SPECTRAL-SPATIOTEMPORAL IMAGING OF CARDIAC ELECTRICAL ACTIVITY

CROSS-REFERENCE TO RELATED APPLICATIONS

This application is based on, claims priority to, and incorporates herein by reference in its entirety, U.S. Provisional application Ser. No. 61/817,710, filed Apr. 30, 2013, and entitled, "SYSTEMS AND METHODS FOR NONINVASIVE SPECTRAL-SPATIOTEMPORAL IMAGING OF CARDIAC ELECTRICAL ACTIVITY."

STATEMENT REGARDING FEDERALLY SPONSORED RESEARCH

This invention was made with government support under R01 HL080093 awarded by the National Institutes of Health, and CBET-0756331 awarded by the National Science Foundation. The government has certain rights in the invention.

BACKGROUND

The present disclosure relates generally to systems and methods for cardiac electrophysiology imaging and measurements. More particularly, the disclosure relates to systems and methods for noninvasive imaging of cardiac electrical activity, including atrial electrical activity.

Atrial arrhythmias, especially atrial fibrillation (AF), are gaining growing clinical concerns due to the prevalence within the population and the fact that they put the patient at risk of heart failure and stroke, and increase the rate of mortality. As the most common super-ventricular arrhythmia, the mechanisms of AF have long been controversial and debatable. Previous research gave rise to the hypothesis that localized sites in the atria with high-frequency activities are closely linked to sources maintaining AF, in both animal experiments and human studies. A number of studies also characterized the spatial-temporal organization of paroxysmal AF as spectrally hierarchical, featured by a left-to-right frequency gradient. Current endocardial mapping techniques are able to determine the electrograms, activation patterns, and above-mentioned frequency distribution during AF, using either non-contact mapping or sequential electroanatomical mapping methods. Although widely used clinically, this technique is invasive, requires sedation, and is limited in simultaneous and continuous bi-atrial mapping. The invasive nature substantially conflicts with the clinically-desired diagnostic information about the AF mechanism in intact human heart with continuous recording.

To address the above-mentioned issues, research interests have been focused on noninvasive analysis of surface electrocardiography (ECG). The body surface potential mapping technique is able to illustrate atrial electrical activities on the torso surface by using high-density surface electrodes. It has been used to depict surface activation wave fronts and evaluate spatial complexity and spectral variability during AF. Unfortunately, body surface potential mapping only provides information about the actual atrial electrical activities in an indirect manner, in a sense that it is over the surface of the torso instead of over the heart.

Another area of intense research interest is to combine the surface recordings and subject-specific heart-torso model to reconstruct the cardiac electrical activities by solving the inverse problem. A typical example of applications in atria is to image epicardial and endocardial activation isochrones during paced rhythm data and atrial flutter. Another study reconstructed epicardial activation maps of atrial flutter and AF by estimating epicardial potential. However, these methods do not depict the electrophysiological properties of AF from a spectral perspective and thus not able to identify the critical high-frequency sites from body surface potential mapping (BSPM).

Accordingly, there is a continuing need for systems and methods to provide accurate, insightful, and clinically-useful information related to atrial arrhythmias, especially AF.

SUMMARY OF THE INVENTION

The present disclosure overcomes the aforementioned drawbacks by providing systems and methods for imaging atrial electrical activity using a source imaging technique in combination with frequency analysis to non-invasively provide information regarding atrial activation sequences, as well as the spectral characteristics. For example, images of the distribution of equivalent current density (ECD) can be reconstructed from body surface potential maps (BSPMs) using a physical-model based noninvasive cardiac electrical imaging (NCEI) approach. Activation sequences, dominant frequency (DF), and critical high-frequency sites that potentially maintain atrial fibrillation (AF) can be derived subsequently from the ECD distributions. The systems and methods of the present disclosure can provide information about and distinguish between atrial electrical activity during sinus rhythm, flutter, and AF from noninvasive BSPMs.

In accordance with one aspect of the disclosure, a system is provided for non-invasively generating a report of cardiac electrical activities of a subject. The system includes a first input configured to receive anatomical information acquired from a region of interest (ROI) in the subject including a heart of the subject and a second input configured to receive physiological information acquired from the subject related to the heart of the subject. The system also includes a processor configured to determine, using the physiological information, equivalent current densities (ECDs) and determine, using the ECDs, at least one of activation sequences (AS) and dominant frequency (DF) information for the heart of the subject. The processor is further configured to generate a map of the heart of the subject using the anatomical information and the at least one of AS and DF information illustrating a spatial distribution of electrical activation information over at least a portion of the heart of the subject.

In accordance with another aspect of the disclosure, a method is disclosed for non-invasively generating a report of cardiac electrical activities of a subject. The method includes accessing medical imaging data including information about a heart of a subject and accessing cardiac electrical information about the heart of the subject. The method also includes determining, using a processor, equivalent current densities (ECDs) from the cardiac electrical information and determining, using the ECDs and a processor, at least one of activation sequences (AS) and dominant frequency (DF) information for the heart of the subject. The method further includes generating a map of the heart of the subject using the medical imaging data and the at least one of AS and DF information illustrating a spatial distribution of electrical activation information over at least a portion of the heart of the subject.

In accordance with yet another aspect of the disclosure, a system is disclosed for non-invasively generating a report of cardiac electrical activities of a subject. The system includes a first input configured to receive medical imaging information acquired using at least one of a magnetic resonance imaging system and a computed tomography system, wherein the medical imaging data includes information from a region of interest (ROI) in the subject including a heart of the subject. The system also includes a second input configured to receive cardiac electrical activation information acquired from the subject using a plurality of electrodes arranged outside the ROI. The system further includes a processor configured to determine, using the cardiac electrical activation information, equivalent current densities (ECDs) and assemble the ECDs into time-course ECD information. The processor is further configured to analyze a spectrum of the time-course ECD information to determine peaks for spectral characteristics of atrial fibrillation (AF) and correlate the spectral characteristics of AF with potential electrical sources of the AF. The processor is further configured to generate a report indicating the potential electrical sources of the AF spatially registered with the medical imaging data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 9A and 9B are examples of an imaging report in accordance with the present disclosure showing imaged AFL reentrant circuit, where solid lines represent propagation wave front in RA, dashed lines indicate that in LA, an arrow is included pointing to tricuspid isthmus representing linear ablation at this site and AFL=atrial flutter; CSO=coronary sinus ostium; MA=mitral annulus; and TA=tricuspid annulus.

FIG. 11 illustrates a comparison of results obtained from different ECG lengths.

DETAILED DESCRIPTION OF THE INVENTION

As will be described, the present disclosure is able to leverage and/or collect and correlate information from one or more hardware systems to provide information regarding atrial electrical activity. For example, hardware systems may be used to collect data related to an activation imaging technique in combination with frequency analysis to non-invasively provide information regarding atrial activation sequences, as well as the spectral characteristics. For example, as will be described herebelow, systems for collecting body surface potential maps (BSPMs) and other medical imaging systems, such as computed tomography (CT) or magnetic resonance imaging (MRI) systems, can be utilized to create a physical-model based noninvasive cardiac electrical imaging (NCEI) approach and provide images of the distribution of equivalent current density (ECD). Activation sequences, dominant frequency (DF), and critical high-frequency sites that potentially maintain atrial fibrillation (AF) can be derived subsequently from the ECDs. The systems and methods of the present disclosure can provide information about and distinguish between atrial electrical activity during sinus rhythm, flutter, and AF from noninvasive BSPMs.

Figure 1:
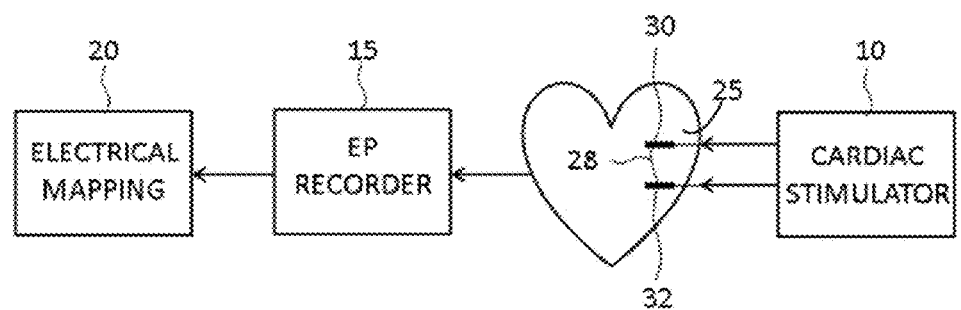
FIG. 1 is a block diagram showing one embodiment of a body-surface mapping system in accordance with the present disclosure.

For example, referring to FIG. 1, complex arrhythmias, such as atrial fibrillation or ventricular tachycardia, may record the spontaneous arrhythmias or concurrently use a cardiac stimulator system 10 in combination with an electrophysiology (EP) recording system 15 and an electrical mapping system 20 in study of a subject's heart 25. The cardiac stimulator system 10 can be used to direct an application of a stimulator or pace signal 28 by the cardiac stimulator system 10 via catheters 30 and 32 at various anatomical features or locations of the heart 25. The EP recording system 15 can be used to record surface electrocardiogram signals and various other patient vital physiological data of the subject during the cardiac stimulation procedure or during spontaneous arrhythmias. The electrical mapping system 20 can be used to image an electrical activation on either a pseudo-anatomical model of the heart 25, or on a previously acquired anatomical image of the heart 25 based on the output of EP recording system 15. The output of the electrical mapping system 20 can be used to document the patient case, and may also be used by the physician to help determine the appropriate position/location of the arrhythmic substrate relative to various locations of the heart 25.

Figure 2:
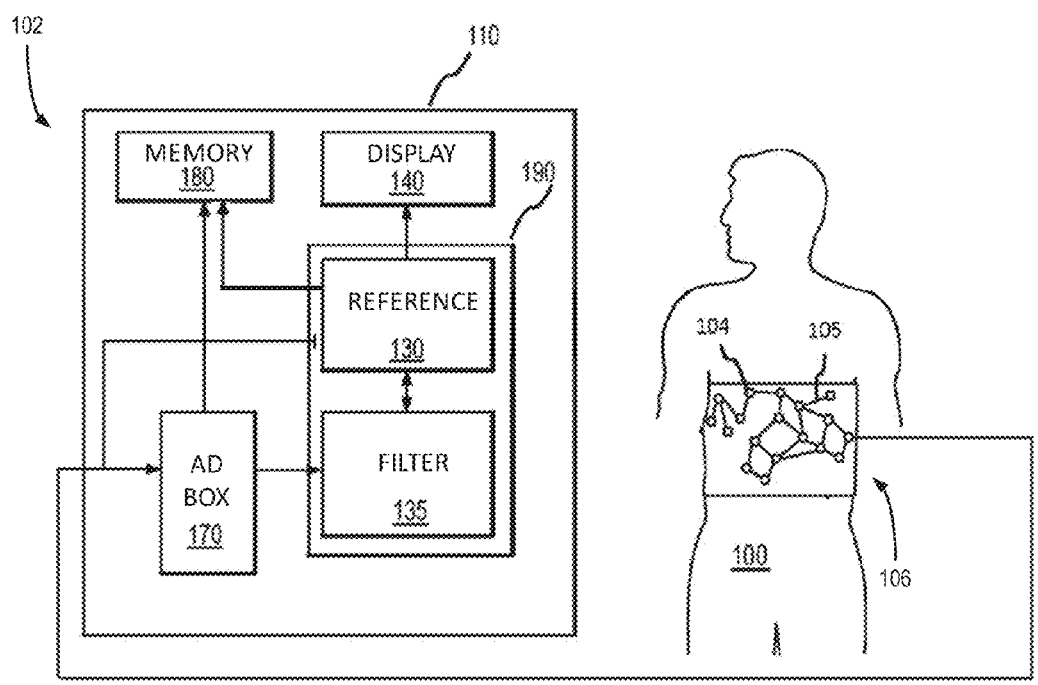
FIG. 2 is a block diagram of a system for recording body surface potential maps (BSPMs) of a subject in accordance with the present disclosure.

As another example, referring to FIG. 2, a system for recording body surface potential maps (BSPMs) of a subject 100, referred to hereinafter as body-surface mapping system 102, is shown. As shown, the system 102 includes a plurality of electrodes 104 connected through electrical connections 105 and configured to be coupled to a torso 106 of the subject 100. The electrodes 104 may be supported by a garment, a large patch, an elastic belt, or the like. The body-surface mapping system 102 may have any number of electrodes. In some systems the system 102 may have at least 64 electrodes or even 256 or more electrodes.

The BSPM recording system 110 may include an A/D convertor box 170, a memory storage system 180, and signal processing system 190, and an output system 140. The electrodes 104 are connected to an A/D box that is part of BSPM recording system 110. The A/D box 170 as part of the BSPM recording system 110 is provided to convert the analog signal as recorded by the electrodes 104 to digital signals. The memory system 180 may be a data storage server and/or a portable flash drive to store massive BSPM data which is digitized by the A/D box 170. The output system 140 may be a display to communicate information directly to a user and/or connection to communicate with other systems. The signal processing unit 190 receives the digital BSPM data from A/D box 170, filters the signal with digital filter unit 135 to remove baseline drifting and artifacts, and refers the signal with the Wilson Center Terminal (WCT) in the reference unit 130. The output of the signal processing unit 190 is then transferred to display 140 and to memory 180 for storage.

Figure 3A:
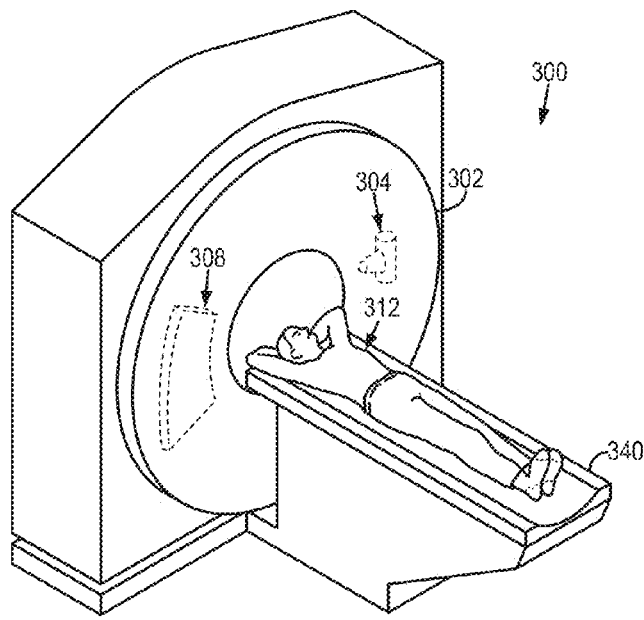
FIGS. 3A and 3B are a perspective view and a block diagram, respectively, of a system for performing computed tomography (CT) imaging in accordance with the present disclosure.
Figure 3B:
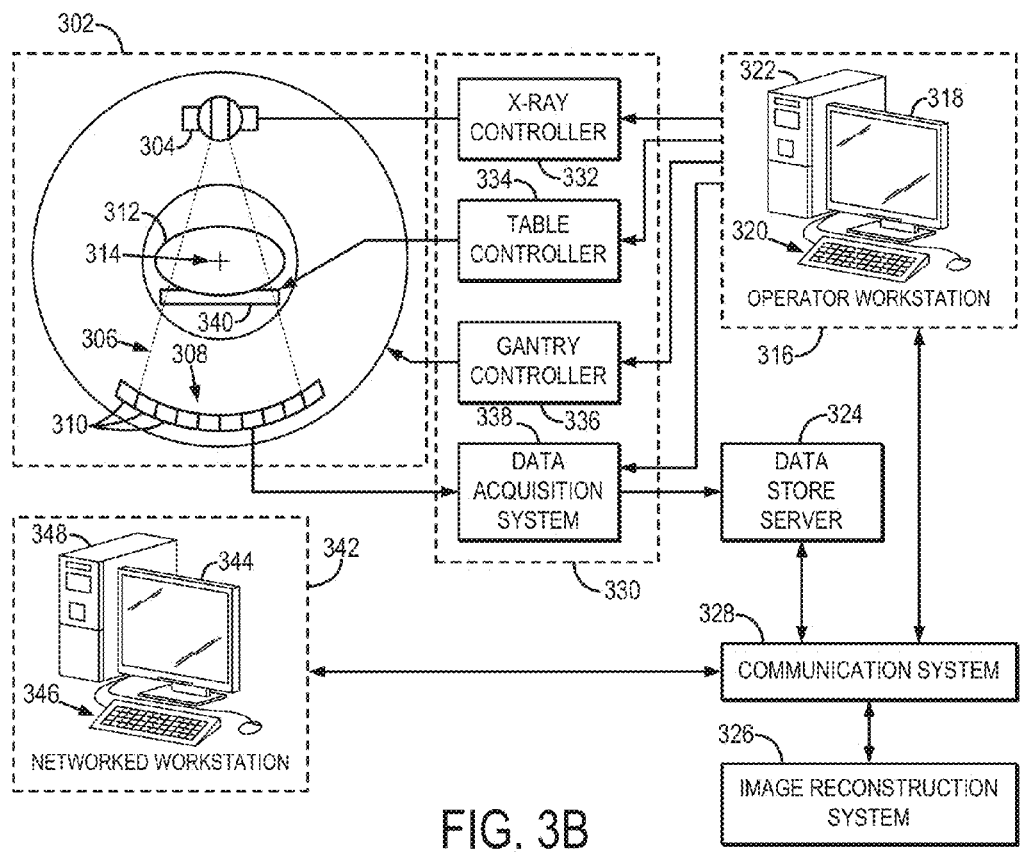

Another system that may be used in accordance with the present disclosure is a computed tomography (CT) imaging system. Referring particularly now to FIGS. 3A and 3B, an example of an x-ray computed tomography ("CT") imaging system 300 is illustrated. The CT system includes a gantry 302, to which at least one x-ray source 304 is coupled. The x-ray source 304 projects an x-ray beam 306, which may be a fan-beam or cone-beam of x-rays, towards a detector array 308 on the opposite side of the gantry 302. The detector array 308 includes a number of x-ray detector elements 310. Together, the x-ray detector elements 310 sense the projected x-rays 306 that pass through a subject 312, such as a medical patient or an object undergoing examination, who is positioned in the CT system 300. Each x-ray detector element 310 produces an electrical signal that may represent the intensity of an impinging x-ray beam and, hence, the attenuation of the beam as it passes through the subject 312. In some configurations, each x-ray detector 310 is capable of counting the number of x-ray photons that impinge upon the detector 310. During a scan to acquire x-ray projection data, the gantry 302 and the components mounted thereon rotate about a center of rotation 314 located within the CT system 300.

The CT system 300 also includes an operator workstation 316, which typically includes a display 318; one or more input devices 320, such as a keyboard and mouse; and a computer processor 322. The computer processor 322 may include a commercially available programmable machine running a commercially available operating system. The operator workstation 316 provides the operator interface that enables scanning control parameters to be entered into the CT system 300. In general, the operator workstation 316 is in communication with a data store server 324 and an image reconstruction system 326. By way of example, the operator workstation 316, data store sever 324, and image reconstruction system 326 may be connected via a communication system 328, which may include any suitable network connection, whether wired, wireless, or a combination of both. As an example, the communication system 328 may include both proprietary or dedicated networks, as well as open networks, such as the internet.

The operator workstation 316 is also in communication with a control system 330 that controls operation of the CT system 300. The control system 330 generally includes an x-ray controller 332, a table controller 334, a gantry controller 336, and a data acquisition system 338. The x-ray controller 332 provides power and timing signals to the x-ray source 304 and the gantry controller 336 controls the rotational speed and position of the gantry 302. The table controller 334 controls a table 340 to position the subject 312 in the gantry 302 of the CT system 300.

The DAS 338 samples data from the detector elements 310 and converts the data to digital signals for subsequent processing. For instance, digitized x-ray data is communicated from the DAS 338 to the data store server 324. The image reconstruction system 326 then retrieves the x-ray data from the data store server 324 and reconstructs an image therefrom. The image reconstruction system 326 may include a commercially available computer processor, or may be a highly-parallel computer architecture, such as a system that includes multiple-core processors and massively parallel, high-density computing devices. Optionally, image reconstruction can also be performed on the processor 322 in the operator workstation 316. Reconstructed images can then be communicated back to the data store server 324 for storage or to the operator workstation 316 to be displayed to the operator or clinician.

The CT system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 316, or in a different facility, such as a different healthcare institution or clinic.

The networked workstation 342, whether within the same facility or in a different facility as the operator workstation 316, may gain remote access to the data store server 324 and/or the image reconstruction system 326 via the communication system 328. Accordingly, multiple networked workstations 342 may have access to the data store server 324 and/or image reconstruction system 326. In this manner, x-ray data, reconstructed images, or other data may exchanged between the data store server 324, the image reconstruction system 326, and the networked workstations 342, such that the data or images may be remotely processed by a networked workstation 342. This data may be exchanged in any suitable format, such as in accordance with the transmission control protocol (TCP), the internet protocol (IP), or other known or suitable protocols.

Figure 4:
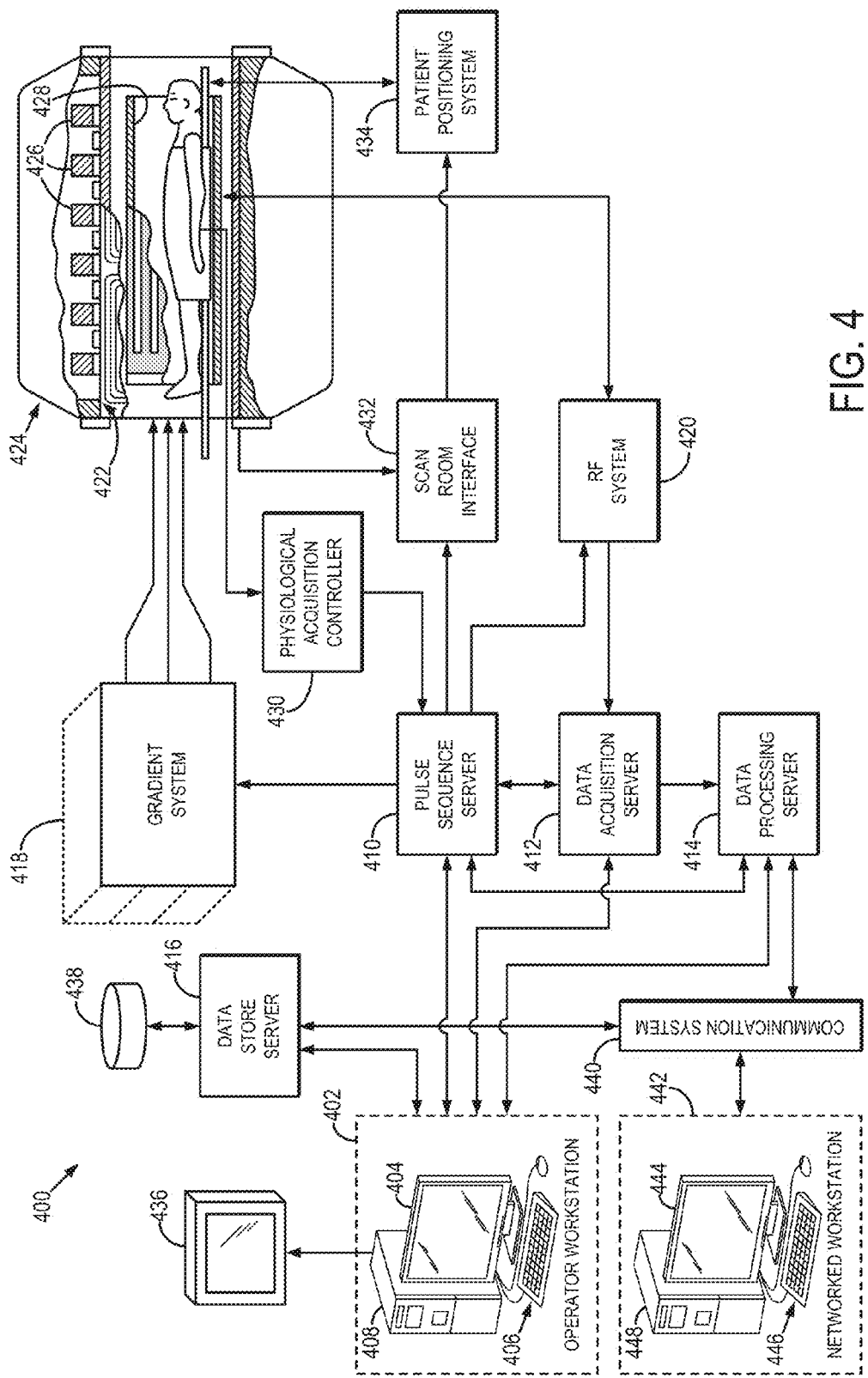
FIG. 4 is a block diagram of a system for performing magnetic resonance imaging (MRI) in accordance with the present disclosure.

Another example of a system that may be used in accordance with the present disclosure is an MRI system. Referring particularly now to FIG. 4, an example of a magnetic resonance imaging (MRI) system 400 is illustrated. The MRI system 400 includes an operator workstation 402, which will typically include a display 404; one or more input devices 406, such as a keyboard and mouse; and a processor 408. The processor 408 may include a commercially available programmable machine running a commercially available operating system. The operator workstation 402 provides the operator interface that enables scan prescriptions to be entered into the MRI system 400. In general, the operator workstation 402 may be coupled to four servers: a pulse sequence server 410; a data acquisition server 412; a data processing server 414; and a data store server 416. The operator workstation 402 and each server 410, 412, 414, and 416 are connected to communicate with each other. For example, the servers 410, 412, 414, and 416 may be connected via a communication system 440, which may include any suitable network connection, whether wired, wireless, or a combination of both. As an example, the communication system 440 may include both proprietary or dedicated networks, as well as open networks, such as the internet.

The pulse sequence server 410 functions in response to instructions downloaded from the operator workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil (not shown in FIG. 4), in order to perform the prescribed magnetic resonance pulse sequence. Responsive magnetic resonance signals detected by the RF coil 428, or a separate local coil (not shown in FIG. 4), are received by the RF system 420, where they are amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the scan prescription and direction from the pulse sequence server 410 to produce RF pulses of the desired frequency, phase, and pulse amplitude waveform. The generated RF pulses may be applied to the whole-body RF coil 428 or to one or more local coils or coil arrays (not shown in FIG. 4).

The RF system 420 also includes one or more RF receiver channels. Each RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components $M=\sqrt{I^2+Q^2}$ and the phase of the received magnetic resonance signal may also be determined according to the following relationship $$\varphi = \tan^{-1}\left(\frac{Q}{I}\right).$$

The pulse sequence server 410 also optionally receives patient data from a physiological acquisition controller 430. By way of example, the physiological acquisition controller 430 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, such that no data is lost by data overrun. In some scans, the data acquisition server 412 does little more than pass the acquired magnetic resonance data to the data processor server 414. However, in scans that require information derived from acquired magnetic resonance data to control the further performance of the scan, the data acquisition server 412 is programmed to produce such information and convey it to the pulse sequence server 410. For example, during prescans, magnetic resonance data is acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also be employed to process magnetic resonance signals used to detect the arrival of a contrast agent in a magnetic resonance angiography ("MRA") scan. By way of example, the data acquisition server 412 acquires magnetic resonance data and processes it in real-time to produce information that is used to control the scan.

The data processing server 414 receives magnetic resonance data from the data acquisition server 412 and processes it in accordance with instructions downloaded from the operator workstation 402. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 414 are conveyed back to the operator workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the operator workstation 402. The operator workstation 402 may be used by an operator to archive the images, produce films, or send the images via a network to other facilities.

The MRI system 400 may also include one or more networked workstations 442. By way of example, a networked workstation 442 may include a display 444; one or more input devices 446, such as a keyboard and mouse; and a processor 448. The networked workstation 442 may be located within the same facility as the operator workstation 402, or in a different facility, such as a different healthcare institution or clinic.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may exchanged between the data processing server 414 or the data store server 416 and the networked workstations 442, such that the data or images may be remotely processed by a networked workstation 442. This data may be exchanged in any suitable format, such as in accordance with the transmission control protocol (TCP), the internet protocol (IP), or other known or suitable protocols.

Using one or more of the above-described or other systems, the present disclosure provides systems and methods for data acquisition, processing, and imaging cardiac activity using an activation imaging technique in combination with frequency analysis to non-invasively provide information regarding atrial activation sequences, as well as the spectral characteristics.

Figure 5:
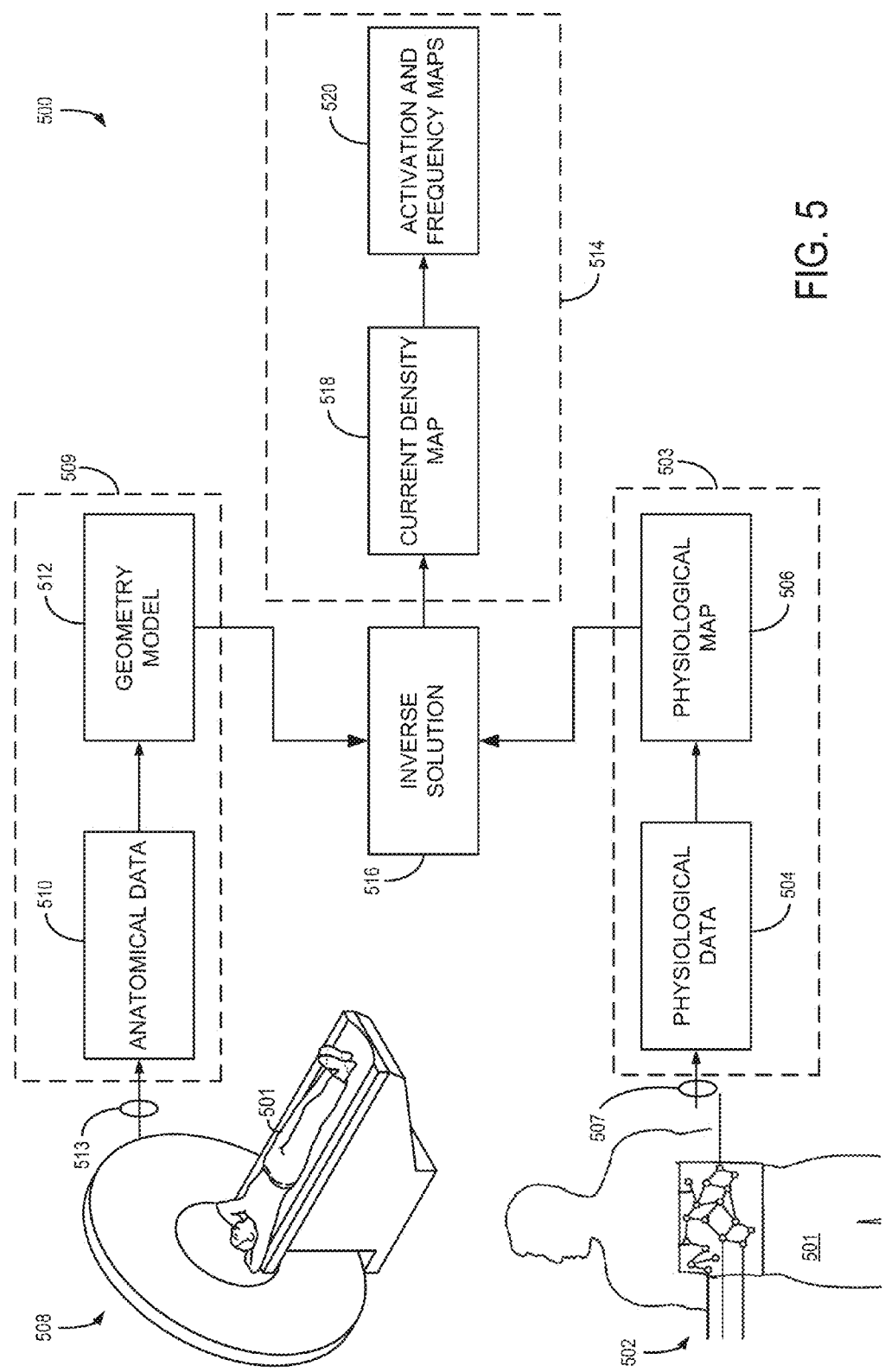
FIG. 5 is an operational schematic diagram of a system for noninvasive cardiac electrical imaging (NCEI) for analyzing cardiac electrical activity using an activation imaging technique in combination with frequency analysis to non-invasively provide information regarding atrial activation sequences, as well as the spectral characteristics.

By way of example, a system and process 500 for physical-model based noninvasive cardiac electrical imaging technique (NCEI) in accordance with the present disclosure is illustrated in the block schematic provided in FIG. 5. In particular, data from multiple of the above-described system is acquired from a subject 501. The system 500 may be formed of a few sub-systems. For example, at least one sub-system 502 is designed to communicate with a computer or processor system 503 to acquire physiological data 504 from the subject 501 and produce physiological maps 506. To this end, the computer or processor system 503 may include an input 505 configured to receive acquired or stored data. For example, as described above, such sub-systems 502 may include a body-surface mapping system or be capable of performing body-surface mapping. To this end, the physiological data 504 may include ECG data and the physiological maps 506 may include BSPMs.

For example, when a subject is in a resting state (e.g., supine with smooth breathing), BSPMs can be measured on the anterior and posterior chest using a multi-channel electrocardiogram (ECG) measurement system, such as a 208-channels BioSemi Active-Two measurement system with a sampling rate of 2048 Hz (with 400 Hz cut off frequency of low pass filter) and a 24 bit analog-to-digital converter. The location of electrode positions can be recorded using a radio frequency digitizer (e.g., Fastrak, Polhemus Inc., Vermont).

Also, a sub-system 508 may be used to acquire anatomical data that is communicated to a computer or processor system 509 to produce anatomical data 510. For example, the sub-system 508 may be a CT or MRI system, such as described above. To this end, data acquired by the sub-system 508 may be used to form a geometry model 512. Specifically, the computer or processor system 509 may include an input 513 to receive information from the sub-system 508. The data acquired through the input 513 may be raw imaging data that is processed or reconstructed by the computer or processor system 509, such as acquired from MRI or CT data. Also, the data received through the input 513 may be reconstructed images. Furthermore, the computer or processor system 509 may form part of a MRI or CT imaging system. In any case, CT or MRI data can be used to obtain images of the subject 501 about a region of interest (ROI) selected to obtain subject-specific heart-torso geometry. As such, the geometry model 512 may be a heart-torso geometry model.

When using CT, images can be obtained using an intravenous contrast agent. A continuous volume scanning can be performed with a slice thickness of a few mm such as 6 mm from the level of collar bone down to the lower abdomen, which can be used to reconstruct the geometry of heart, lung and torso, and thus to build a completed whole-torso model. An additional scan can optionally be performed from the great vessel level down to the diaphragm or lower with slice thickness of 1 mm or less (such as 0.4 mm). This image data can then be used to build a refined heart model. The in-plane resolution of the CT scans can be fixed, such as at 512×512 pixels. Breath holds can be used to avoid respiratory artifacts. Continuous ECG can also be monitored and used for cardiac gating the CT scanner.

MRI scans can also be performed and, similar to the CT scan, two sets of images can be acquired: one covering from great vessel level down to the diaphragm with a slice thickness of 1 mm, which can be obtained to get a detailed heart model; and the other covering from the collar bone down to the lower abdomen with a slice thickness of 5 mm, which can be used to reconstruct the completed torso model. The physiological data 504, such as ECG signals, can also be monitored and used to gate the MRI scanning process.

The computer or processor systems 503, 509 may be integrated with each other and/or the sub-systems 502, 508. Also, the computer or processor systems 503, 509 may include memories, storage mediums, user interfaces, displays, and the like to acquire, store, process, communicate, and manipulate information acquired from the sub-systems 502, 508.

When using two sets of MRI/CT images, the heart and torso images can be coupled based on known cardiac anatomical landmarks, such as the apex, and co-registration errors can be minimized with the assistance of commercialized software, such as Curry 6.0 (Curry 6.0, Neuroscan, North Carolina) or other software. To this end, the anatomical data 510 and/or geometry model 512 can be co-registered with the physiological maps 506 or BSPMs. Coregistration errors can be minimized with the assistance of commercialized software such as Curry 6.0 or other software.

The technique is an approach to model cardiac electrical activities 514 in terms of equivalent current densities (ECDs). The ECDs, which are considered as equivalent electrical "sources", are obtained by mathematically solving a spatial-temporal linear inverse problem by coupling the body surface potential maps and heart-torso boundary element model (BEM). Thus, as will be described, the present disclosure can provide an inverse solution 516 to this problem and derive cardiac electrical activity information 514, such as current density maps 518 and cardiac activation and frequency maps 520, which may be ECD maps and activation sequences (AS) and dominant frequency (DF) maps, respectively.

In particular, based on the Bidomain theory, such as described by W. T. Miller and D. B. Geselowitz, "Simulation studies of the electrocardiogram. I. The normal heart." Circ Res. vol. 43, pp. 301-315, August 1978, the ECD distribution can be considered as the cardiac electrical "source" accounting for the extracellular potential "field". The concept is expressed in the following equation:

$$\nabla \cdot [(G_i(r) + G_e(r))\nabla \phi_e(r,t)] = \nabla \cdot \vec{j}_{eq}(r,t) \qquad (1);$$

Where $G_i(r)$ and $G_e(r)$ are the intracellular and extracellular effective conductivity tensors at location r respectively, and $\phi_e(r,t)$ is the extracellular potential at location r and at time t. By definition, the ECD $\vec{j}_{eq}(r,t)$ at location r and time t is proportional to the spatial gradient of local transmembrane potential (TMP) $\phi_m(r,t)$, as shown by Eq. (2):

$$\vec{j}_{eq}(r,t) = -G_i(r)\nabla \phi_m(r,t) \qquad (2).$$

The relationship between the ECD and the spatial gradient of TMP can be used in accordance with the present disclosure to derive the activation time. For a given myocardial site, the activation time can be considered as the time instant when the excitation wavefront passes across the site. At the time point of excitation, there is a considerable TMP amplitude that only exists across the excitation wavefront, which means that a cell at its activation time is featured by the maximum TMP spatial gradient. Based on Eq. (2), the amplitude of ECD $\vec{j}_{eq}(r,t)$ is proportional to the spatial gradient of TMP $\nabla \phi_m(r,t)$, thus the activation time $\tau(r)$ at location r can be derived as the time instant at which local ECD reaches its temporal maximum, as expressed by Eq. (3):

$$\tau(r) = \mathrm{argmax}_t \left| \vec{j}_{eq}(r, t) \right|. \tag{3}$$

Such relationship between ECD and the TMP spatial gradient also provides features for the study of DF. As DF can be derived from intra-cardiac bipolar recording and is, in nature, the high-frequency electrical activities during AF, the TMP spatial gradient is an electrophysiological analogue to derive the DF, and so is ECD.

In one non-limiting example, the time course of $\vec{j}_{eq}(r,t)$ can be tapered with a Hanning window to set the edge value to zero, and processed with a 3 Hz-15 Hz band-pass filter. A Fast Fourier transform (FFT) can be performed on the time course of ECD at each given atrial location. The biatrial DF map can then be reconstructed from the frequency corresponding to the highest peak in the power spectrum. The primary maximum DF (DFmax) site can be defined as maximal DF surrounded by an >=20 percent decreasing frequency gradient. The secondary DFmax site can be defined similarly with secondary-high DF value and a >=20 percent frequency gradient. Both primary and secondary DFmax sites can be considered as DF sites acting as potential drivers maintaining the AF.

Figure 6:
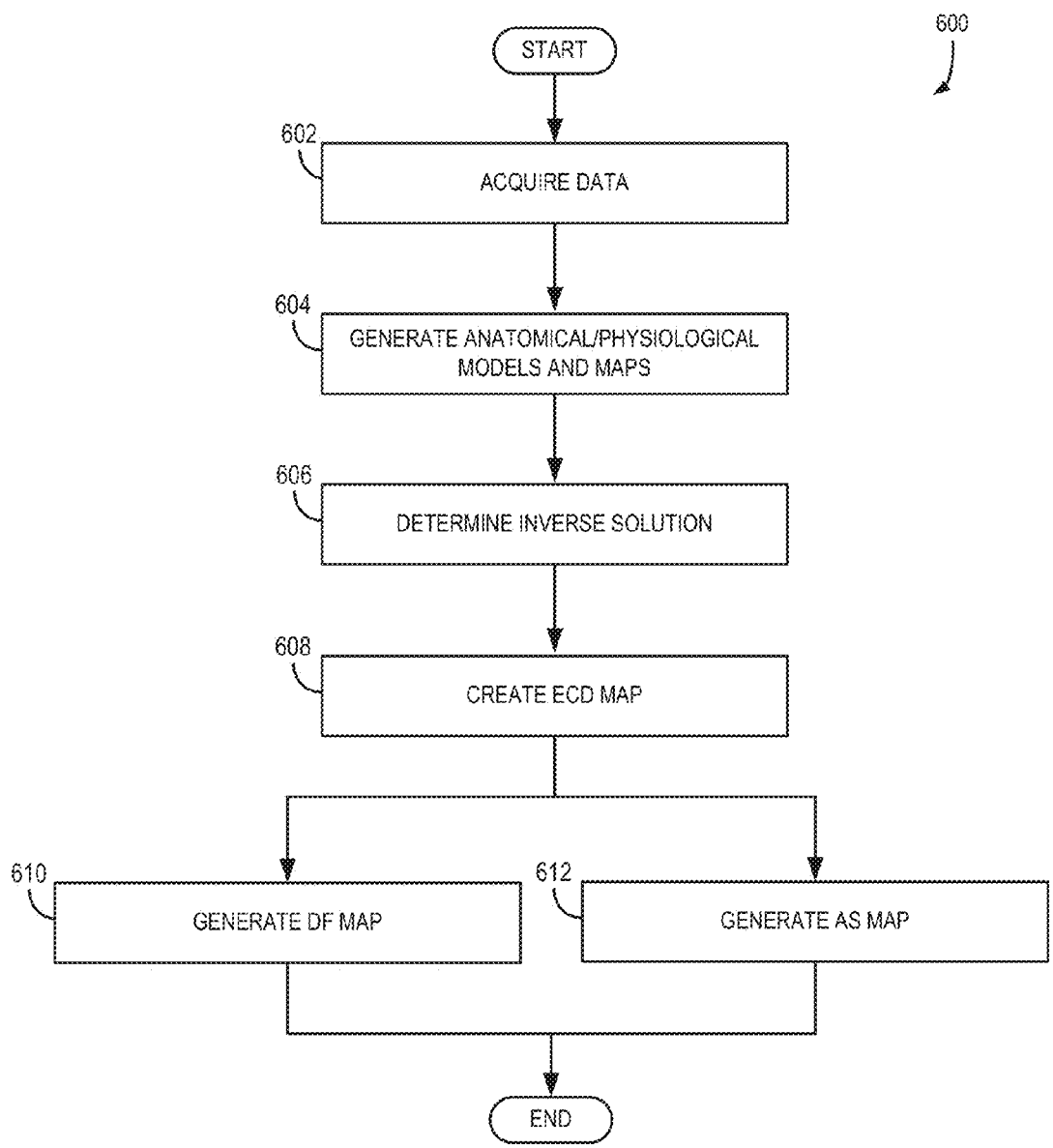
FIG. 6 is a flow chart setting forth an example of a process for performing an NCEI technique.

In particular, referring to FIG. 6, a process 600 for NCEI begins at process block 602 with data acquisition, such as described above. At process block 604, anatomical and physiological models and maps are created. For example, a commercial software package Curry 6.0 (Compumedics, Charlotte, N.C.), can be used for segmentation to build the subject-specific realistic geometry heart-torso model from CT/MRI images. This computer model includes heart, lungs, blood cavities, and chest surface. This heart-torso model can be exported for further forward and inverse computation in a software package developed in MATLAB2007a (MathWorks, Natick, Mass.). In one non-limiting example, the atrium was discretized into thousands of grid points. The spatial resolution of the atrial models was 3 mm. A distributed ECD model was used to represent the cardiac electrical sources. Regardless of the specific model, given a tessellated geometrical heart-torso model and the prior knowledge of the electrical conductivity of relevant tissues and organs, the extracellular potentials measurable over the body surface can be linearly related to the ECD distribution by using the boundary element method (BEM). The linear relationship can be described by:

$$\Phi(t) = LJ(t) \tag{4};$$

where $\Phi(t)$ is an M×1 column vector of body surface potentials from M body surface electrodes at time t, J(t) is a 3N×1 column vector of ECD distribution from N myocardial grid points, and L is the M×3N source-to-sensor transfer matrix. Thus, at process block 606, this linear inverse problem can be solved using the weighted minimum norm (WMN) estimation, such as described by J. Z. Wang et al., "Magnetic source images determined by a lead-field analysis: The unique minimum-norm least-squares estimation," IEEE Trans. Biomed. Eng., vol. 39, no. 7, pp. 665-675, July 1992, which is incorporated herein by reference, and which minimizes the following objective function:

$$\min_{J(t)} (\|\Phi(t) - LJ(t)\|_2^2 + \lambda \|WJ(t)\|_2^2) \tag{5};$$

where W is the Kronecker product of, for example, a 3×3 identity matrix L and a diagonal matrix $\Omega$ whose component is calculated from the lead field matrix L. $\lambda$ is the regularization parameter, which can be determined by the L-curve method, such as described by P. C. Hansen, "Analysis of discrete ill-posed problems by means of the L-curve," SIAM Rev, vol. 34, pp. 561-580, December 1992, which is incorporated herein by reference. Therefore, at process block 608 and as illustrated in FIG. 5, current density maps 516 can be created that may be, more particularly, an estimation of the ECD distribution at time t of location r. Thereafter, as will be described, activation and frequency maps 520, which may be images or maps illustrating and dominant frequency (DF) at process block 610 and activation sequences (AS) at process block 612 can be provided.

To evaluate the performance, for each subject, the AS from each independent beat can be averaged and taken as a referenced AS. The intra-subject consistency and inconsistency between the referenced AS and each independently imaged AS can be quantified by correlation coefficient (CC) and relative error (RE):

$$CC = \frac{\sum_{i=1}^{n}(AT_i^E - \overline{AT^E})(AT_i^R - \overline{AT^R})}{\sqrt{\sum_{i=1}^{n}(AT_i^E - \overline{AT^E})^2} \times \sqrt{\sum_{i=1}^{n}(AT_i^R - \overline{AT^R})^2}}; \tag{6}$$

and $$RE = \sqrt{\frac{\sum_{i=1}^{n}(AT_i^E - AT_i^R)^2}{\sum_{i=1}^{n}(AT_i^R)^2}}; \tag{7}$$

where n is the total number of source points in the atriums, $AT_i^E$ and $AT_i^R$ are the estimated activation time and referenced activation time of the i-th source point, and $\overline{AT^E}$ and $\overline{AT^R}$ are the averaged estimated and referenced activation time over all n atrial points, respectively.

A non-limiting example of data analysis is now described. As noted above, subject-specific geometry models can be constructed from subjects' MRI/CT images. For example, these models can be constructed using the Curry 6.0 software mentioned above. The endocardial current density sources can be linearly related to BSPM by a boundary element model built from individual MRI/CT images. The source surface can be defined as the endocardium of the LA and RA. For the segmentation of the atria, important anatomical structures, like the pulmonary veins (PV), superior vena cava (SVC), inferior vena cava (IVC), tricuspid annulus (TA) and mitral annulus (MA), can be indentified and segmented out.

Due to the thinness of atrial wall, the electrical activities can be assumed to occur over a 2D surface rather than the 3D volume. The 2D atrial ECD distributions can, thus, be reconstructed by coupling measured BSPM with a BEM model, using an embedded minimum norm least square (MNLS) inverse solution. From the peak criterion described by Z. Liu, et al., in "Noninvasive reconstruction of three-dimensional ventricular activation sequence from the inverse solution of distributed equivalent current density," *IEEE Trans Med Imaging*, 2006; 25:1307-1318 and incorporated herein by reference, the activation time, T, at a given location, i, can be determined as the time instant corresponding to the maximum value of ECD waveform J(i, t):

$$\tau(i) = \underset{t \in T}{\mathrm{argmax}}(|J(i, t)|). \quad (8)$$

A selected number of beats of normal atrial activation (NAA) and of atrial flutter (AFL) can be analyzed, and the corresponding activation sequences reconstructed. For a given subject, the imaged activation sequences from each independent beat can be averaged and taken as the referenced activation sequence. The intra-subject consistency and inconsistency between the referenced activation and each independently imaged activation can then be quantified by correlation coefficient (CC) and relative error (RE).

Figure 7:
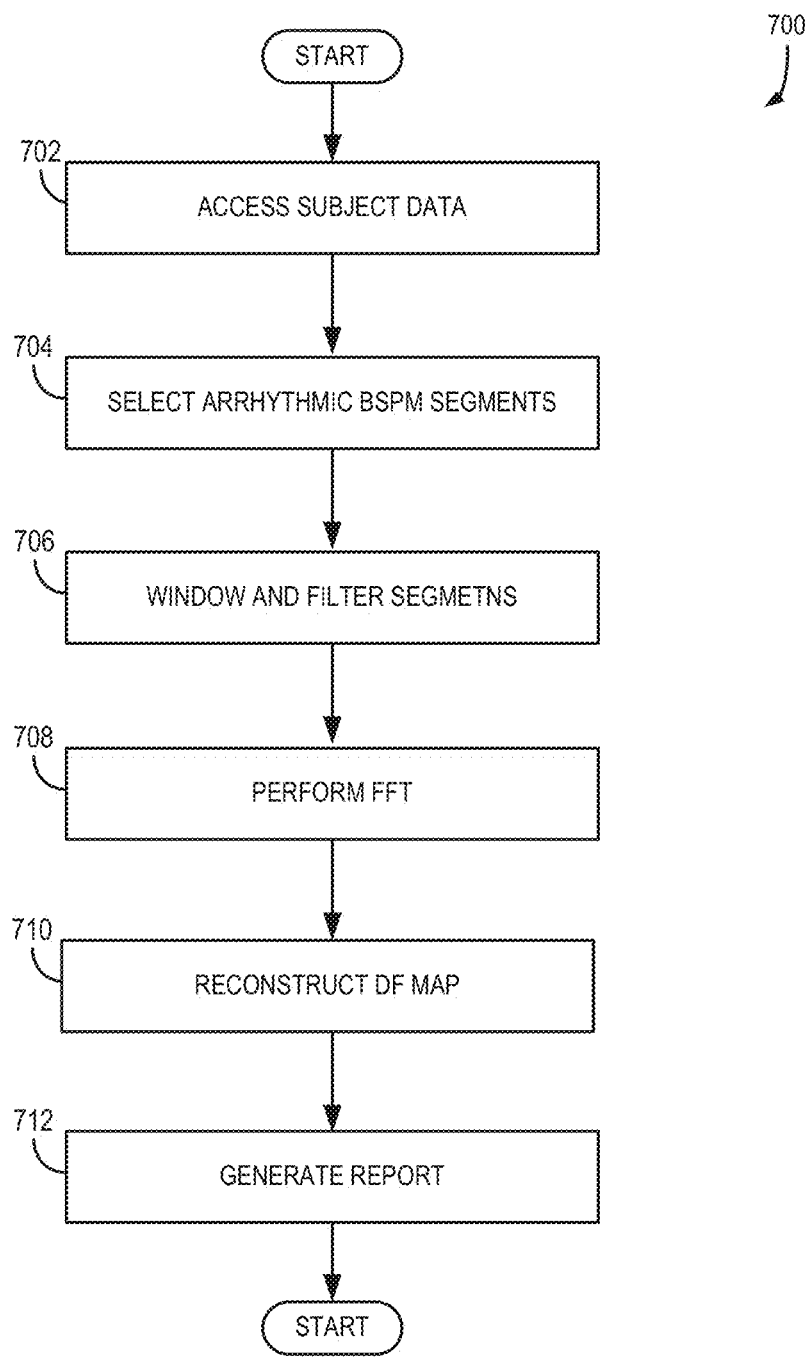
FIG. 7 is a flow chart setting forth an example of a process for generating reports as part of an NCEI technique.

Specifically, referring now to FIG. 7, at process block 702, a subject's data is accessed, either in real time from an ongoing acquisition or from a storage medium. For subject's with recorded AF, the ECDs can be estimated a follows. At process block 704, a number of segments of arrhythmic BSPMs, such as 15 segments, are selected. Then at process block 706, the segments are tapered, such as with a Hanning window, to set the edge value to zero and the windowed segments processed with, for example, a 3 Hz-15 Hz band-pass filter.

At process block 708, an FFT can be performed on the time course of ECD at each given atrial location. At process block 710, a biatrial DF map can be reconstructed from, for example, the frequency corresponding to the highest peak in the power spectrum. The primary maximum DF (DFmax) site is defined as maximal DF surrounded by a frequency gradient that decreases by twenty percent or more. The secondary DFmax site is defined similarly with secondary-high DF value and a frequency gradient of twenty percent or more. Both primary and secondary DFmax sites are considered as critical DF sites acting as potential sources maintaining the AF. Thus, at process block 712 a report can be provided that indicates NAA and AFL relative to the selected data.

Figure 8B:
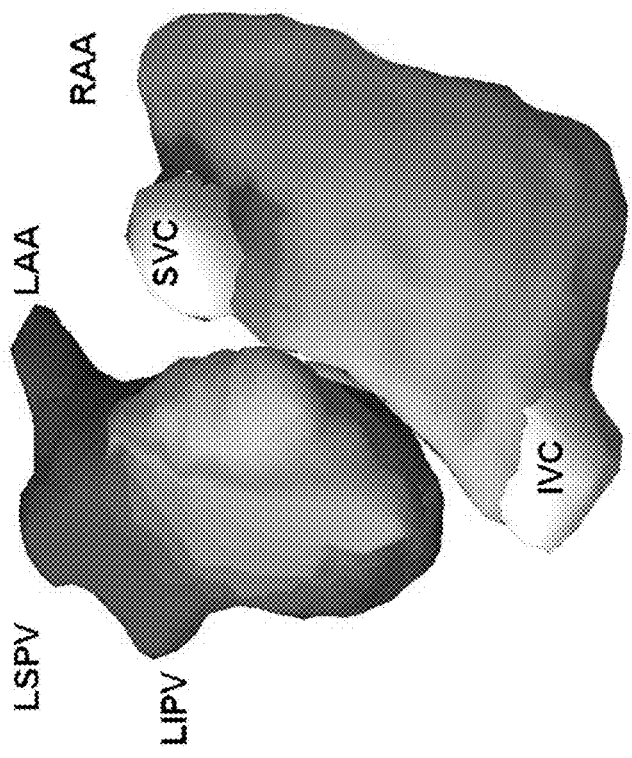
FIGS. 8A and 8B are examples of an imaging report in accordance with the present disclosure showing an activation sequence of NAA on a subject, where LA=left atrium; LIPV=left inferior pulmonary vein; LSPV=left superior pulmonary vein; NAA=Normal atrial activation; RA=right atrium; RIPV=right inferior pulmonary vein; and RSPV=Right superior pulmonary vein.
Figure 8A:
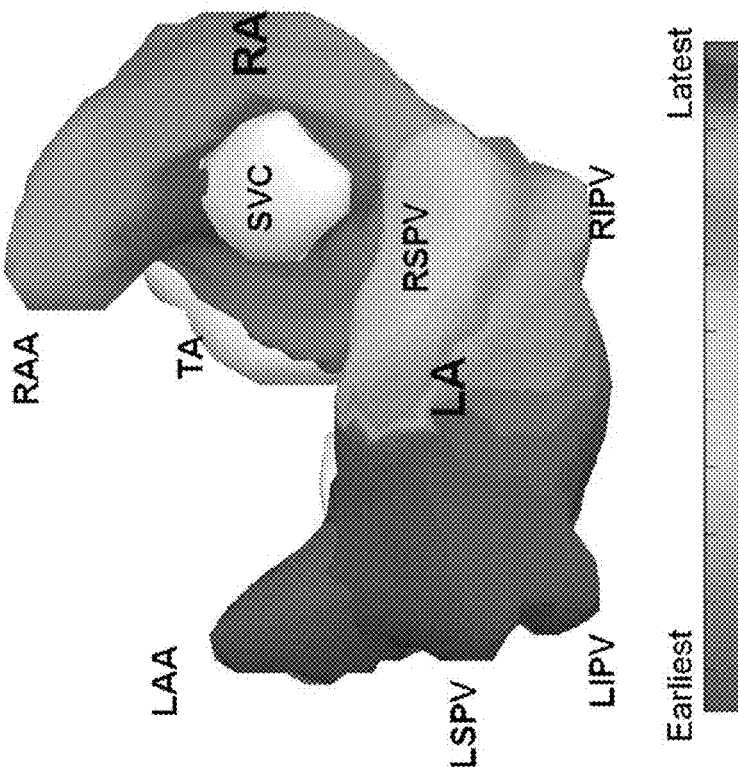

In a non-limiting example, NAAs of healthy subjects were reconstructed from a total of 56 beats of sinus rhythms. BSPMs during P-wave were coupled with subject-specific heart-torso geometry to image the atrial activation sequence. For example, FIGS. 8A and 8B shows one representative example of NAA obtained from a subject relative to a superior view (FIG. 8A) and a posterior-oblique view (FIG. 8B). The earliest activation arises in right atrium from the right border of SVC, which is corresponding to the anatomic location of sinoatrial node. The excitation then propagates to the rest of right atrium (RA) and to the left atrium (LA), and finally reaches the LA appendage. The activation sequences reconstructed from the subjects are in good coherence with the referenced activation sequences, with a mean CC of 0.91 and a RE of 0.13 for all analyzed beats. Table 1 summaries the averaged CC and RE for each healthy subject. The results are also consistent with direct recording from isolated human hearts as reported in literature.

TABLE 1

| Subject # | Rhythm | # of beats | Averaged length of P wave | CC | RE |
| --- | --- | --- | --- | --- | --- |
| 1 | AFL | 15 | 210 ± 10 ms | 0.85 ± 0.06 | 0.19 ± 0.05 |
| 2 | SR | 16 | 102 ± 4 ms | 0.92 ± 0.01 | 0.13 ± 0.014 |
| 3 | SR | 12 | 98 ± 3 ms | 0.89 ± 0.06 | 0.16 ± 0.016 |
| 4 | SR | 15 | 106 ± 2 ms | 0.91 ± 0.05 | 0.12 ± 0.026 |
| 5 | SR | 13 | 103 ± 3 ms | 0.91 ± 0.03 | 0.13 ± 0.011 |
| Mean (Healthy subject) | SR | 14 ± 1.8 | 102 ± 3.3 ms | 0.91 ± 0.01 | 0.135 ± 0.017 |

That is, Table 1 above shows a data from a quantitative comparison between imaged activation sequence and referenced activation sequence, where AFL=atrial flutter; CC=correlation coefficient; RE=relative error; and SR=sinus rhythm.

Referring now to FIGS. 9A and 9B, the feasibility of NCEI to image AFL is illustrated in a subject with typical type 1 flutter. As shown in FIG. 9A, the ECG is characterized by saw-tooth atrial waveform at average 285 beats/min with a cycle length of 210 ms. A total of 15 beats of AFL were analyzed. More particularly, FIG. 9A depicts one cycle of imaged counter-clockwise typical AFL. The imaged reentrant circuit ascends from the tricuspid isthmus near the coronary sinus ostium (CSO), forming a septal wave front traveling upward through the septum. It then divides into two broad limbs: one spreads anteriorly into the area between the SVC and the superior TA; the other wave front spreads posteriorly between SVC and IVC. The two wave fronts then fuse and descend along the RA free-wall, and finally enter the isthmus between TA and IVC at the end of the reentry circuit. The tricuspid isthmus is identified as the critical zone. The LA activation does not involve the reentry circuit. The LA activation initiates from the inferior septum, indicating the trans-septal activation by the inferior CS-LA junction, then propagates along the anterior and posterior LA. FIG. 9B shows another cycle of the imaged AFL in similar pattern with FIG. 9A.

The AFL activation pattern as shown in FIG. 9 is obtained from one subject without patient-specific intracardiac recording of the AFL at this point. Overall, the imaged major reentry circuit is in good consistency with the previously reported results from direct intracardial mapping study of typical atria flutter. The location of the identified critical zone also correlates well with the findings reported in literature. The AFL activation patterns obtained from 15 different beats of BSPMs are in good agreement with the referenced activation, quantified by a CC of 0.85 and a RE of 0.19 (Table 1). All of the 15 imaged cycles show a counter-clockwise circulating wave front confined to RA and a critical zone localized at the tricuspid isthmus. In clinical procedure, the AFL was abolished with linear ablation at tricuspid isthmus in close vicinity with the imaged critical sites. Note that this is a non-limiting example of imaging AFL in a patient.

In another non-limiting example, the BSPMs were measured on subjects with paroxysmal AF. A total of 15 segments of AF (average length 460±52 ms) were sequentially picked up from AF ECG. In order to eliminate the impact of T-wave and QRS and to obtain signals containing sufficient spatiotemporal electrical information. Each segment is a greater than or equal to 400 ms fibrillatory period starting from the end point of T-wave and ended before the onset of QRS (T-Q segment), and is hereby defined as T-Q AF. To perform the analysis of different AF length, the ventricular components of BSPM can be removed by subtracting the BSPM with a QRS template that is defined from averaged QRS beats. Thus the DF maps can be reconstructed from an unlimited length of BSPM with merely AF component. In another non-limiting example, the DF map was reconstructed from 5-s AF BSPM, and the result was compared with that obtained from T-Q segment with a length of 420 ms.

Figure 10A:
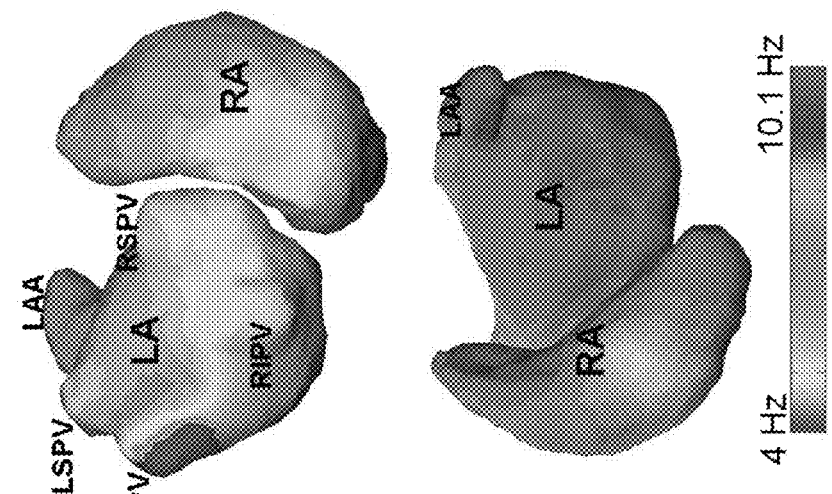
FIGS. 10A, 10B and 10C are examples of and imaging report in accordance with the present disclosure showing imaged DF maps with different patterns of distributions.
Figure 10B:
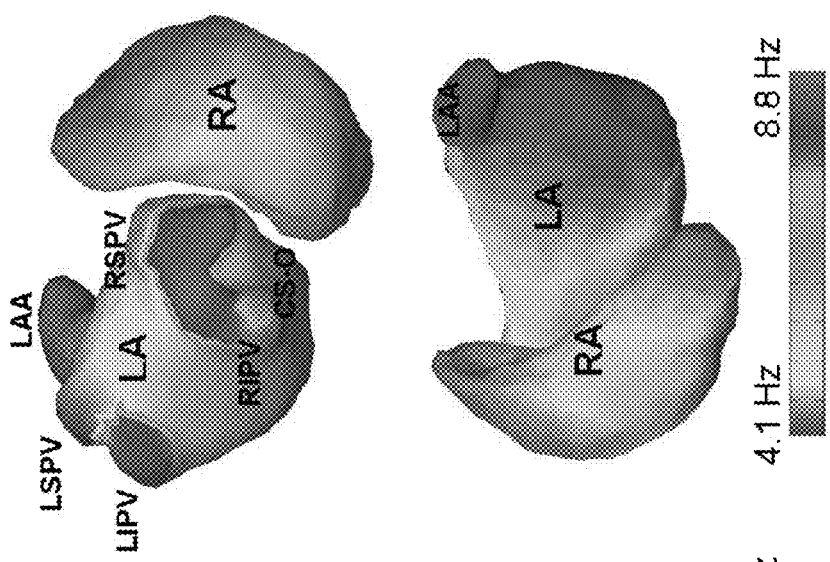
Figure 10C:
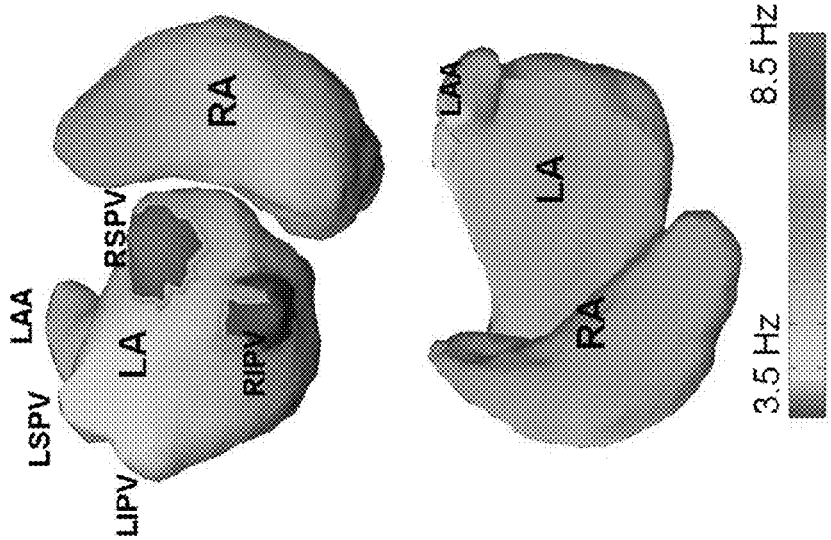

In one of the studied subjects, the distributions of primary DFmax and secondary DFmax can be categorized into three types, referring to FIG. 10: (1) RSPV and RIPV as the primary/secondary DFmax, referring to FIG. 10A, imaged from 7 out of the segments; (2) RSPV, RIPV, and LIPV as the DFmax sites, referring to FIG. 10B, in 4 out of 15 segments, referring to FIG. 10B; (3) LIPV as the only DFmax site, referring to FIG. 10C, from 4 out of 15 segments. The dynamic transitions of the DFmax sites are also captured by NCEI. The results obtained from one subject are summarized in Table 2 below.

ment. For the 7 AF segments of type-1 distribution, the primary DFmax was holding at RSPV (9.9±0.95 Hz), implying the potential of RSPV being the predominant high-frequency source maintaining the ongoing fibrillation. In AF segments with type-3 distribution, the primary DFmax was at the LIPV only (9.1±0.93 Hz), suggesting that it might be another major arrhythmogenic source. The primary DFmax site wanders between RSPV, RIPV and LIPV in type-2 AF segments. LSPV was not identified as a critical DFmax site (5.7±0.98 Hz) for any AF segment, either primary or secondary. On average, a significant left-to-right frequency gradient is presented among the mean DFs at PV/LA junction, CSO and posterior RA (7.48±1.2 Hz, 5.1±0.97, 4.6±0.81 Hz, respectively), which is consistent with intracardiac findings. Moreover, in all the analyzed AF segments, the DF obtained at each PV is higher than that at the CSO, and DF at CSO is greater than the posterior RA, implying the presence of such DF gradient is stable and consistent even in different AF segments in paroxysmal patient. Overall, the NCEI reports indicate RSPV, RIPV, and LIPV as the important DFmax sites potentially maintaining the fibrillation and images a representative left-to-right DF gradient typical in paroxysmal AF. In clinical treatment, the AF was eliminated with circumferential PV isolations, which isolate the RSPV, RIPV, LIPV and LSPV that are indicated as associated with high-frequency AF activities in the above-mentioned example.

TABLE 2

| Period | AF segments | Time (s) | Type | Length (ms) | Critical DFmax sites | DF (Hz) of critical DFmax | DF at CSO (Hz) | DF at RA (Hz) |
|---|---|---|---|---|---|---|---|---|
| T1 | T1-1 | 7.2 | 3 | 428 | LIPV | 9.22 | 5.49 | 5.02 |
|    | T1-2 | 16.1 | 2 | 420 | RSPV | 8.81 | 6.19 | 4.76 |
|    |      |      |   |     | RIPV | 7.98 |      |      |
|    |      |      |   |     | LIPV | 7.74 |      |      |
|    | T1-3 | 19.6 | 2 | 504 | RSPV | 7.79 | 5.13 | 3.95 |
|    |      |      |   |     | RIPV | 7.60 |      |      |
|    |      |      |   |     | LIPV | 10.26 |     |      |
|    | T1-4 | 24.6 | 3 | 450 | LIPV | 10.10 | 4.44 | 4.33 |
| T2 | T2-1 | 9.5  | 1 | 449 | RSPV | 9.44 | 3.98 | 3.52 |
|    |      |      |   |     | RIPV | 8.99 |      |      |
|    | T2-2 | 10.8 | 1 | 496 | RSPV | 10.98 | 5.34 | 4.23 |
|    |      |      |   |     | RIPV | 10.87 |     |      |
|    | T2-3 | 14.2 | 1 | 564 | RSPV | 8.42 | 5.50 | 5.41 |
|    |      |      |   |     | RIPV | 7.98 |      |      |
|    | T2-4 | 18.2 | 1 | 403 | RSPV | 10.79 | 6.94 | 6.44 |
|    |      |      |   |     | RIPV | 11.16 |     |      |
|    | T2-5 | 29.9 | 2 | 439 | RSPV | 9.44 | 6.49 | 5.46 |
|    |      |      |   |     | RIPV | 9.56 |      |      |
|    |      |      |   |     | LIPV | 9.44 |      |      |
|    | T2-6 | 43.7 | 3 | 554 | LIPV | 9.11 | 4.33 | 4.42 |
|    | T2-7 | 58.6 | 3 | 419 | LIPV | 7.83 | 4.86 | 4.27 |
| T3 | T3-1 | 11.0 | 1 | 410 | RSPV | 10.1 | 3.78 | 3.77 |
|    |      |      |   |     | RIPV | 9.74 |      |      |
|    | T3-2 | 20.2 | 2 | 426 | RSPV | 10.09 | 3.63 | 3.40 |
|    |      |      |   |     | RIPV | 9.85 |      |      |
|    |      |      |   |     | LIPV | 9.74 |      |      |
|    | T3-3 | 33.6 | 1 | 429 | RSPV | 8.96 | 5.00 | 4.77 |
|    |      |      |   |     | RIPV | 8.96 |      |      |
|    | T3-4 | 37.3 | 1 | 516 | RSPV | 10.26 | 5.13 | 5.03 |
|    |      |      |   |     | RIPV | 10.16 |     |      |

That is, Table 2 above shows results obtained from 15 segments of paroxysmal AF, where AF=atrial fibrillation; CSO=coronary sinus ostium; DF=dominant frequency; LIPV=left inferior pulmonary vein; LSPV=left superior pulmonary vein; RIPV=right inferior pulmonary vein; and RSPV=right superior pulmonary vein.

A total of 15 segments of AF (average length 460±52 ms) were sequentially picked up from ECG recorded at 3 independent time periods T1, T2, and T3 during the T-Q seg- Previous studies suggest a greater than one second length of AF electrogram for reconstructing DF from intracardiac mapping. Yet, it is challenging to meet such requirement when it comes to body surface mapping, as the ventricular components is always mixed with the atrial activities. To allow the analysis of AF with different length, the ventricular components of BSPM can be removed by subtracting the BSPM with a QRS template that is defined from averaged QRS beats. In particular, FIG. 11 provides a comparison of results obtained with different ECG lengths. The left panel shows imaged DF distribution based on T-Q AF with a length of 0.42 s, and the right panel shows DF distribution based on the 5-s AF segment containing the much shorter T-Q AF. Similar DF patterns are clearly observed from different ECG lengths, showing that the method described here is stable against ECG length variation, and that the system is able to perform analysis on different ECG length based on the clinician's need.

Current clinical intracardiac techniques have certain restrictions in terms of spatial resolution, simultaneous and continuous bi-atrial mapping, time consumption and the prerequisite of stable hemodynamics. On the other hand, the above-descried NCEI approach is capable of reconstructing biatrial DF maps and activation sequences noninvasively from BSPMs on a beat-to-beat basis with a sufficient resolution. For complex arrhythmia such as AF, it can provide pre-operative mapping of arrhythmic activities over a long period, which can assist in closely reviewing the temporal variation in human arrhythmias and optimizing the ablation procedure. Therefore, the NCEI techniques described herein can aid in clinical catheter ablation of AF and advance current understanding of the mechanisms of the underlying arrhythmia.

Therefore, systems and methods are provided to utilize noninvasive electrical source imaging techniques in combination with frequency analysis to image the atrial activation sequence and spectral characteristics of atrial arrhythmias from BSPM. NCEI can be used to image focal atrial arrhythmia originating from an ectopic focus. Moreover, NCEI is capable of delineating the activation pattern of more complex atrial arrhythmia and identify the critical zone for ablation on a single-beat basis. For instance, the reentrant cycle and critical zone of AFL can be successfully imaged in good coherence with direct endocardial recordings of previous studies. Further still, NCEI is feasible in reconstructing DF maps and identifying the sites with high-frequency activity acting as a potential sources maintaining AF by using spectral analysis.

In one example, the critical high-frequency sites were identified at RSPV, RIPV and LIPV. A significant LA-to-RA frequency gradient was also imaged in this example. The DF distributions were repeated over independent AF segments. The NCEI is able to image such repetition as well as the dynamic transitions between different patterns. The result shows a good agreement with the clinical outcome of circumferential PV isolation and is further supported by direct endocardial mapping study. These findings indicate that NCEI is feasible in locating initiation of ectopic beat, reconstructing activation sequence of both focal and complex atrial arrhythmias, and imaging arrhythmogenic substrate featured by high-frequency activities during AF.

The paroxysmal AF data presented here reveals underlying AF mechanisms and highlight the dynamic transition of DFmax locations. Specifically, the single or multiple DFmax sites featured by high-frequency periodical electrical activities restricted in pulmonary veins are consistent with the previous findings from clinical studies and animal experiments. The existence of sustaining left-to-right DF gradients is consistent with the spatiotemporal organization of paroxysmal AF. The observation of temporal variation as well as spatial stability of the critical DFmax sites agree with the spatio-temporal complexity of AF itself and is further supported by previous findings. The abovementioned observations show localized sites of high-frequency electrical activities with a corresponding frequency hierarchy as the mechanism of AF in patients studied.

The systems and methods of the present invention have clinical implications for assisting the ablation of persistent and long standing persistent AF. Non-paroxysmal AF is ablated with a much lower termination rate in clinical intervention. Compared with the paroxysmal AF, non-paroxysmal AF is characterized by the spatiotemporal disorganization, a loss of the hierarchical frequency gradient, and a biatrial dispersion of DFmax. It is also suggested that failure of termination might be due to the untargeted critical DFmax sites dispersed at both atria. The complexity of persistent and long-standing persistent AF results in the challenge of optimal intra-operative mapping. Knowledge regarding the spatio-temporal distributions of these underlying substrates is important and can be used to improve the outcome of an ablation procedure. While clinical sequential mapping is limited in this aspect, NCEI techniques can assist in localizing these critical DFmax sites, image the spatiotemporal variation of DFmax before clinical intervention and provide evaluation on the surgery outcome soon after.

The NCEI techniques also offer ability to further aid in clinical intervention of paroxysmal AF. A certain portion of AF patients with non-PV ectopy foci was reported. The locations of these triggers disperse over LA and RA. Therefore, it is important to identify PV and non-PV initiated Paroxysmal AF and further predict the location of the non-PV triggers. As the DFmax is closely associated with such underlying source maintaining AF, NCEI can be used to characterize locations of the potential high-frequency sources and optimize the ablation strategy pre-operatively and non-invasively.

The NCEI techniques can be utilized to image atrial activation sequence. The NCEI techniques can image atrial arrhythmias of focal as well as reentrant pattern, with high intra-subject consistency and good agreement with clinical ablative outcome. It is contemplated that the NCEI can be used as a complementary tool in clinical practice to offer the diagnostic information in terms of the localization of ectopic foci, the critical zones for ablation and the global activation patterns.

Thus, systems and methods are provided for spectral analysis together with noninvasive cardiac source imaging to reconstruct a spatial distribution of DF and to identify high-frequency sites maintaining AF. These NCEI systems and methods are capable of localizing initiation sites and critical zones, reconstructing a activation sequence of focal and complex atrial arrhythmias, and imaging a DF map as well as high-frequency sources during AF. The NCEI systems and methods provide clinically assistive tools to aid in catheter ablation and to advance current knowledge of the underlying mechanisms of these arrhythmias.

Some non-limiting clinical applications of the present disclosure include localizing and imaging of cardiac electrical activity associated with various cardiac abnormalities; guiding cardiac ablation treatment of arrhythmias or cardiac resynchronization therapy (CRT); localizing origins or drivers of atrial fibrillations and other arrhythmias, including ventricular arrhythmias; and aiding ablation or CRT treatments.

The present invention has been described in terms of one or more preferred embodiments, and it should be appreciated that many equivalents, alternatives, variations, and modifications, aside from those expressly stated, are possible and within the scope of the invention.

We claim:

1. A system for non-invasively generating a report of cardiac electrical activities of a subject, the system comprising:

a first input configured to receive anatomical information acquired from a region of interest in the subject including a heart of the subject;

a second input configured to receive physiological information acquired from the subject related to the heart of the subject;

a non-transitory memory having stored thereon instructions;

a processor configured to access the memory to receive and execute the instructions and, following the instructions, to:

determine, using the physiological information, equivalent current densities (ECDs);

determine, using the ECDs, activation sequences (AS) and dominant frequency (DF) information for the heart of the subject; and generate a map of the heart of the subject using the anatomical information and the AS and DF information illustrating a spatial distribution of electrical information over at least a portion of the heart of the subject.

2. The system of claim 1 wherein the processor is configured to assemble the ECDs into time-course ECD information and analyze a spectrum of the ECD information to determine peaks to generate the DF information.

3. The system of claim 1 wherein the processor is further configured to record body surface potential maps (BSPMs) from the subject and generate a heart-torso boundary element method (BEM) model using the anatomical information.

4. The system of claim 3 wherein the processor is further configured to determine the ECDs by mathematically solving a spatial-temporal linear inverse problem by coupling the BSPM and the heart-torso BEM model.

5. The system of claim 1 wherein the processor is further configured to generate the map to provide atrial electrical activity during sinus rhythm, flutter, and AF.

6. The system of claim 1 wherein the first input is configured to receive the physiological data from a series of electrodes configured to perform at least one of an electrocardiography (ECG) technique and a body surface potential mapping (BSPM) technique.

7. The system of claim 1 wherein the processor is configured treat the ECDs as cardiac electrical sources in an electrical field formed by intracellular and extracellular effective conductivity tensors at locations and extracellular potential at locations and in time.

8. The system of claim 7 wherein the processor is configured to relate the ECD at a given location and at a given time as proportional to a spatial gradient of local transmembrane potential (TMP) and, using a relationship between ECD and TMP, determine the DF information and activation times of the heart of the subject.

9. The system of claim 1 wherein the processor is further configured to generate the map to illustrate a spatial distribution of DF and high-frequency sites maintaining atrial fibrillation (AF).

10. The system of claim 1 wherein the second input is configured to receive anatomical data from at least one of a magnetic resonance imaging system and a computed tomography system.

11. A method for non-invasively generating a report of cardiac electrical activities of a subject, the method comprising:

accessing medical imaging data including information about a heart of a subject;

accessing cardiac electrical information about the heart of the subject;

using a processor in communication with a non-transitory memory having stored thereon instructions that cause the processor to, determine equivalent current densities (ECDs) from the cardiac electrical information;

using the ECDs and the processor, determine activation sequences (AS) and dominant frequency (DF) information for the heart of the subject;

using the processor, generating a map of the heart of the subject using the medical imaging data and the AS and DF information illustrating a spatial distribution of electrical activation information over at least a portion of the heart of the subject; and using a display in communication with the processor, displaying the map of the heart illustrating the spatial distribution of electrical activation information over at least a portion of the heart of the subject.

12. The method of claim 11 further comprising, using the processor to assemble the ECDs into time-course ECD information and analyze a spectrum of the ECD information to determine peaks to generate the DF information.

13. The method of claim 11 further comprising, using the processor to record body surface potential maps (BSPMs) from the subject and generate a heart-torso model using the medical imaging data.

14. The method of claim 13 further comprising, using the processor to determine the ECDs by mathematically solving a spatial-temporal linear inverse problem by coupling the BSPMs and the heart-torso model.

15. A system for non-invasively generating a report of cardiac electrical activities of a subject, the system comprising:

a first input configured to receive medical imaging information acquired using at least one of a magnetic resonance imaging system and a computed tomography system, wherein the medical imaging data includes information from a region of interest (ROI) in the subject including a heart of the subject;

a second input configured to receive cardiac electrical activation information acquired from the subject using a plurality of electrodes arranged outside the ROI;

a non-transitory memory having stored thereon instructions;

a processor configured to access the memory to receive and execute the instructions and, following the instructions, to:

determine, using the cardiac electrical activation information, equivalent current densities (ECDs);

assemble the ECDs into time-course ECD information;

analyze a spectrum of the time-course ECD information to determine dominant frequency (DF) information and peaks for spectral characteristics of atrial fibrillation (AF);

correlate the spectral characteristics of AF and DF information with potential electrical sources of the AF;

generate a report indicating the potential electrical sources of the AF spatially registered with the medical imaging data; and a display to display the report.

16. The system of claim 15 wherein the processor is further configured to determine dominant frequency (DF) information to determine the sources of the AF.

17. The system of claim 16 wherein the processor is configured analyze the spectrum of the time-course ECD information to determine peaks indicative of a DF to determine the DF information.

18. The system of claim 1 wherein the processor is further configured to record body surface potential maps (BSPMs) reflecting cardiac electrical activation information and generate a heart-torso boundary element method (BEM) model using the medical imaging data.

19. The system of claim 17 wherein the processor is further configured to determine the ECDs by mathematically solving a spatial-temporal linear inverse problem by coupling the BSPMs and the heart-torso BEM model.

20. The system of claim 15 wherein the processor is configured treat the ECDs as cardiac electrical sources in an electrical field formed by intracellular and extracellular effective conductivity tensors at locations and extracellular potential at locations and in time.

21. The system of claim 19 wherein the processor is configured to relate the ECDs at a given location and at a given time as proportional to a spatial gradient of local transmembrane potential (TMP) and, using a relationship between ECD and TMP, determine at least one of DF information and activation times of the heart of the subject.

* * * * *